United States Patent
Salvador et al.

(10) Patent No.: US 11,668,759 B2
(45) Date of Patent: Jun. 6, 2023

(54) METHOD OF ANALYZING THE QUALITY OF A BATTERY CELL BY PERFORMING A COMPREHENSIVE QUALITY CHECK ON BATTERY CELLS ASSESSED AS LOW-QUALITY FROM A HIGH-THROUGHPUT QUALITY CHECK

(71) Applicant: GM Global Technology Operations LLC, Detroit, MI (US)

(72) Inventors: James R. Salvador, East Lansing, MI (US); Debejyo Chakraborty, Novi, MI (US); Ryan Curtis Sekol, Grosse Pointe Woods, MI (US); Thomas A. Yersak, Royal Oak, MI (US); Sean R. Wagner, Shelby Township, MI (US); Charles W. Wampler, Birmingham, MI (US); Ronald M. Lesperance, Troy, MI (US); Raffaello Ardanese, Bloomfield Hills, MI (US); Thanh-Son Dao, Rochester Hills, MI (US); Dmitriy Bruder, Clinton Township, MI (US)

(73) Assignee: GM GLOBAL TECHNOLOGY OPERATIONS LLC, Detroit, MI (US)

(*) Notice: Subject to any disclaimer, the term of this patent is extended or adjusted under 35 U.S.C. 154(b) by 134 days.

(21) Appl. No.: 17/350,681

(22) Filed: Jun. 17, 2021

(65) Prior Publication Data
US 2022/0404431 A1 Dec. 22, 2022

(51) Int. Cl.
*G01R 31/396* (2019.01)
*H01M 10/42* (2006.01)
*G01N 30/02* (2006.01)
*G01F 22/00* (2006.01)
*G01N 33/00* (2006.01)
*G01R 31/382* (2019.01)

(52) U.S. Cl.
CPC ........... *G01R 31/396* (2019.01); *G01F 22/00* (2013.01); *G01N 30/02* (2013.01); *G01N 33/0027* (2013.01); *G01R 31/382* (2019.01); *H01M 10/4285* (2013.01); *G01N 2030/025* (2013.01)

(58) Field of Classification Search
None
See application file for complete search history.

(56) References Cited

U.S. PATENT DOCUMENTS

| | | | |
|---|---|---|---|
| 10,014,561 B2* | 7/2018 | Sood | G01N 29/07 |
| 2014/0266060 A1* | 9/2014 | Ying | H02J 7/0048 320/134 |

(Continued)

*Primary Examiner* — Giovanni Astacio-Oquendo
*Assistant Examiner* — Dilara Sultana
(74) *Attorney, Agent, or Firm* — Vivacqua Crane PLLC

(57) ABSTRACT

A method of analyzing the quality of a battery cell includes performing a high-throughput quality check on the battery cell with a quality control system, assessing a quality score to the battery cell, with quality score identifying the battery cell as low-quality or high-quality, and performing a comprehensive quality check on the battery cell if identified as low-quality. The method further includes assessing an enhanced quality score to the battery cell superseding the quality score of the quality control system identifying the battery cell as confirmed low-quality or confirmed high-quality and providing revised production instructions for manufacturing successive battery cells if confirmed low-quality.

13 Claims, 2 Drawing Sheets

(56) References Cited

U.S. PATENT DOCUMENTS

| 2015/0303723 | A1* | 10/2015 | Raghavan | G01R 31/382 |
| | | | | 73/19.01 |
| 2020/0292622 | A1* | 9/2020 | Wu | G01R 31/396 |
| 2020/0358147 | A1* | 11/2020 | Dou | H01M 10/484 |

* cited by examiner

METHOD OF ANALYZING THE QUALITY OF A BATTERY CELL BY PERFORMING A COMPREHENSIVE QUALITY CHECK ON BATTERY CELLS ASSESSED AS LOW-QUALITY FROM A HIGH-THROUGHPUT QUALITY CHECK

INTRODUCTION

The present disclosure relates to a method of analyzing the quality of a battery cell, and more particularly to a method of analyzing the quality of a battery cell by performing a comprehensive quality check on battery cells assessed as low-quality from a high-throughput quality check.

In recent years, the use of electric motors to power vehicles has increased exponentially. To power the electric motors, battery packs comprised of numerous battery cells are utilized. Most battery cells can maintain a charge suitable to power the vehicle over a range of several hundred miles. However, occasionally battery cells are produced of low-quality that are unable to hold a sufficient charge. A common reason for a low-quality battery cell is an insufficient Solid Electrolyte Interphase (SEI) deposited on the anode of the battery cell. The SEI is formed by the reduction of electrolyte solvents, additives, and salts.

Current practices to analyze the quality of battery cells includes performing a discharge capacity check (i.e., checking that the cell provides capacity (measured in amp-hours) that is within a determined specification) and performing an inventory hold and Open Circuit Voltage (OCV) monitoring (which involves holding the inventory and checking for a decrease in OCV over time). While effective, such quality control measures are time intensive (with the potential for large quality spills and the added cost of overhead to store inventory) and data poor (i.e., not diagnostic or prognostic). Other methods of analyzing the quality of battery cells involve analyzing the SEI on the anode. However, the battery cell must be cut open (destroying the battery cell) to analyze the SEI.

Thus, while current quality control systems for analyzing the quality of a battery cell achieve their intended purpose, there is a need for a new and method of analyzing the quality of a battery cell that addresses these issues.

SUMMARY

According to several aspects of the present disclosure, a method of analyzing the quality of a battery cell comprises performing a high-throughput quality check on the battery cell with a quality control system, assessing a quality score to the battery cell, with quality score identifying the battery cell as low-quality or high-quality, and performing a comprehensive quality check on the battery cell if identified as low-quality. The method further comprises assessing an enhanced quality score to the battery cell superseding the quality score of the quality control system identifying the battery cell as confirmed low-quality or confirmed high-quality and providing revised production instructions for manufacturing successive battery cells if confirmed low-quality.

In one aspect, performing a high-throughput quality check on the battery cell with a quality control system is further defined as one of analyzing the cell formation charge data of the battery cell, analyzing the volume of gas within a gas pouch of the battery cell, analyzing the composition of the gas within the gas pouch, and analyzing the battery cell discharge check data.

In another aspect, the quality control system is further defined as a first quality control system and the quality score is further defined as a first quality score, the method further comprising performing a high-throughput quality check on the battery cell with a second quality control system further defined as one of analyzing the cell formation charge data of the battery cell, analyzing the volume of gas within the gas pouch of the battery cell, analyzing composition of the gas within the gas pouch, and analyzing the battery cell discharge check data that was not performed by the first quality control system, and assessing a second quality score to the battery cell, with second quality score identifying the battery cell as low-quality or high-quality.

In another aspect, the method further comprises analyzing the first and second quality scores and assessing a global quality score identifying the battery cell as low-quality or high-quality.

In another aspect, assessing the global quality score occurs prior to performing the comprehensive quality check on the battery cell.

In another aspect, performing the high-throughput quality check on the battery cell with the first quality control system is further defined as analyzing the cell formation charge data of the battery cell and wherein performing the high-throughput quality check on the battery cell with the second quality control system is further defined as analyzing the composition of the gas within the gas pouch, wherein analyzing the cell formation charge data of the battery cell occurs prior to analyzing the composition of the gas within the gas pouch.

In another aspect, performing the high-throughput quality check on the battery cell with the first quality control system is further defined as analyzing the cell formation charge data of the battery cell and wherein performing the high-throughput quality check on the battery cell with the second quality control system is further defined as analyzing the volume of gas within the gas pouch of the battery cell, wherein analyzing the cell formation charge data of the battery cell occurs prior to analyzing the volume of gas within the gas pouch of the battery cell.

In another aspect, performing the high-throughput quality check on the battery cell with the first quality control system is further defined as analyzing the cell formation charge data of the battery cell and wherein performing the high-throughput quality check on the battery cell with the second quality control system is further defined as analyzing the battery cell discharge check data, wherein analyzing the cell formation charge data of the battery cell occurs prior to analyzing the battery cell discharge check data.

In another aspect, performing the comprehensive quality check on the battery cell if identified as low-quality is further defined as performing gas chromatography on the gas within the gas pouch.

In another aspect, performing the comprehensive quality check on the battery cell if identified as low-quality is further defined as performing accelerated cycling test (ACT) through aging and repeated charge and discharge cycling.

In another aspect, providing revised production instructions for manufacturing successive battery cells if confirmed low-quality is further defined as providing instructions for adaptive formation charge parameters.

In another aspect, the method further comprises reintroducing the battery cell into production if the battery cell is confirmed high-quality.

In another aspect, the method further comprises scrapping the battery cell if the battery cell is confirmed low-quality.

According to several aspects of the present disclosure, a method of analyzing the quality of a battery cell comprises performing a high-throughput quality check on the battery cell with a first quality control system, assessing a first quality score to the battery cell, with the first quality score identifying the battery cell as low-quality or high-quality, performing a high-throughput quality check on the battery cell with a second quality control system, and assessing a second quality score to the battery cell, with the second quality score identifying the battery cell as low-quality or high-quality. The method further comprises analyzing the first and second quality scores and assessing a global quality score identifying the battery cell as low-quality or high-quality, performing a comprehensive quality check on the battery cell if identified as low-quality, assessing an enhanced quality score to the battery cell superseding the quality score of the quality control system identifying the battery cell as confirmed low-quality or confirmed high-quality, and providing instructions for adaptive formation charge parameters if the battery cell is confirmed low-quality.

In one aspect, assessing the global quality score occurs prior to performing the comprehensive quality check on the battery cell.

In another aspect, performing the comprehensive quality check on the battery cell if identified as low-quality is further defined as performing gas chromatography on the gas within the gas pouch.

In another aspect, performing the comprehensive quality check on the battery cell if identified as low-quality is further defined as performing ACT through aging and repeated charge and discharge cycling.

In another aspect, the method further comprises scrapping the battery cell if the battery cell is confirmed low-quality.

According to several aspects of the present disclosure, a method of analyzing the quality of a battery cell comprises analyzing a cell formation charge data of the battery cell with a first quality control system, assessing a first quality score to the battery cell, with the first quality score identifying the battery cell as low-quality or high-quality, analyzing a composition of the gas within a gas pouch of the battery cell with a second quality control system, and assessing a second quality score to the battery cell, with the second quality score identifying the battery cell as low-quality or high-quality. The method further comprises analyzing the first and second quality scores and assessing a global quality score identifying the battery cell as low-quality or high-quality, performing a comprehensive quality check on the battery cell if identified as low-quality, assessing an enhanced quality score to the battery cell superseding the quality score of the quality control system identifying the battery cell as confirmed low-quality or confirmed high-quality, and providing instructions for adaptive formation charge parameters if the battery cell is confirmed low-quality.

In one aspect, performing the comprehensive quality check on the battery cell if identified as low-quality is further defined as performing gas chromatography on the gas within the gas pouch.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
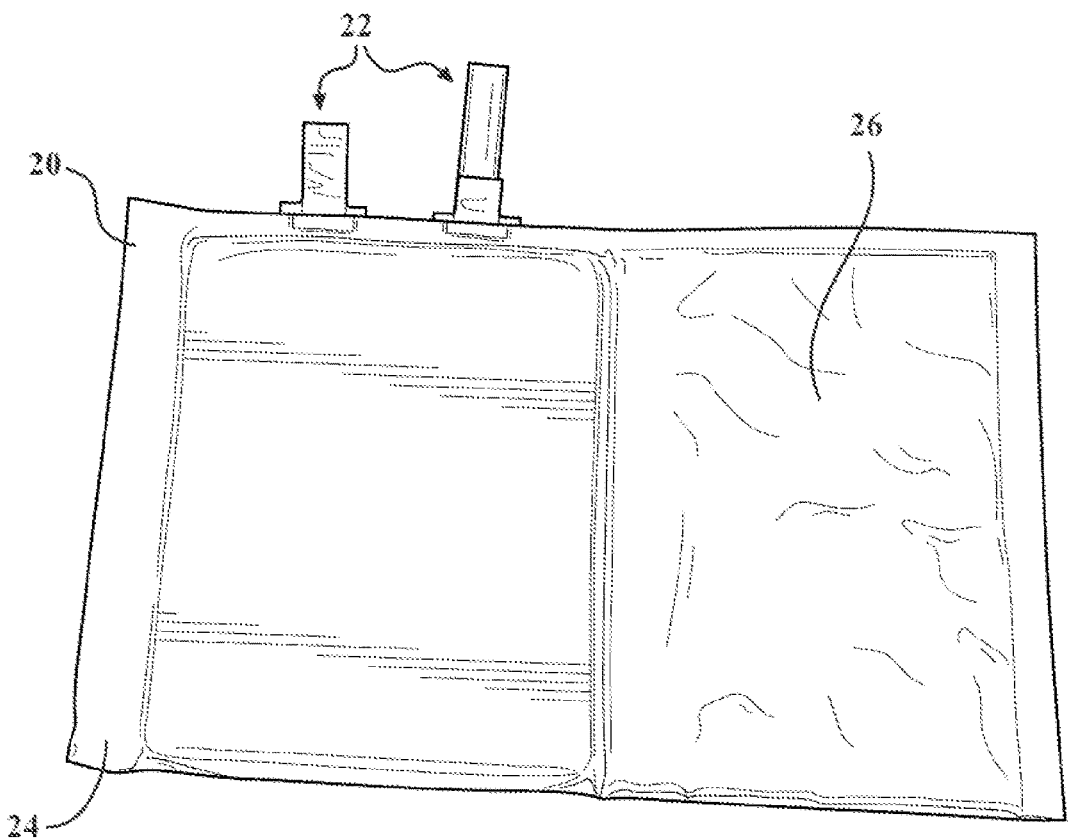
FIG. 1 is a perspective view of one example of a battery cell comprising a gas pouch, with the gas pouch in a deflated configuration.
Figure 2:
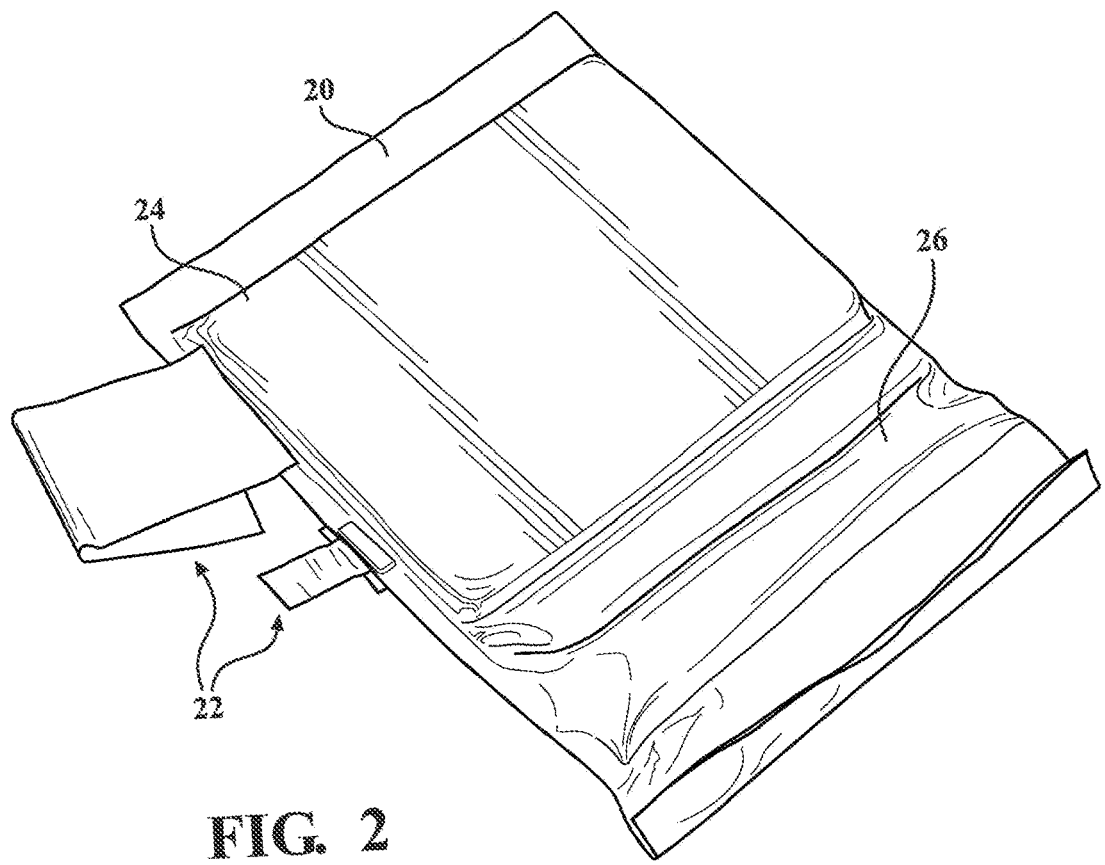
FIG. 2 is a perspective view of the battery cell shown in FIG. 1, with the gas pouch in an inflated configuration.

Referring to FIGS. 1 and 2, according to several aspects of the present disclosure, a battery cell is shown generally at 20. The battery cell 20 is a component of a battery pack. More specifically, the battery pack comprises multiple battery cells 20 that are electrically connected. The common application for such battery cells 20 is in an electric automotive vehicle. However, the battery cells 20 may be utilized in many other applications, such as non-automotive vehicular applications, consumer electronics, etc. The battery cell 20 disclosed herein is a lithium-ion battery cell. The battery cell comprises an electrolyte (not shown) and a pair of electrodes 22 that include an anode and a cathode. The cathode may NCM, NCMA, LMO, LFP, combinations thereof or any like material. The anode may comprise graphite, SiOx, Si, combinations thereof or any like material. The electrolyte may be carbonate based with a fluorinated Li salt. However, battery cells of different chemistries may be utilized.

The battery cell 20 disclosed herein may undergo numerous steps to produce the active battery cell 20. Although steps may vary between different types of battery cells, the battery cell 20 shown herein is produced by first preparing an electrode slurry (not shown) of active material, binder, and conductive agents that are mixed in specific mass ratios. Next, the electrode slurry is coated on the collectors and dried. During a calendering process, the porous electrodes 22 are compressed by driving the electrodes 22 through rollers (not shown). The electrodes 22 are then cut or punched into strips that are wound or stacked together with a separator (not shown). The electrodes 22 (comprising an anode and a cathode) are then placed in a sleeve 24 (more specifically, within a cavity defined by the sleeve 24). During a cell formation process, an electrolyte is injected into the cavity. The electrolyte permeates and fills pores within the electrodes 22. A current is then applied to the electrodes 22 by first applying a constant current to a predetermined first voltage limit, then applying a second constant current to a second voltage limit, and then holding the voltage at the second voltage limit for a predetermined length of time. When the current is applied, the voltage is left to drift according to the charge states of the anode and the cathode.

During the cell formation process, a Solid Electrolyte Interphase (SEI) is deposited on the anode. The SEI (not shown) is formed by the reduction of electrolyte solvents, additives, and salts. The reduction of electrolyte occurs at characteristic voltages and is accompanied by production of gasses which must be vented from the cavity. To this end, the battery cell 20, as shown in FIGS. 1 and 2, further comprises a gas pouch 26 in fluid communication with the cavity. The gas pouch 26 is configured to expand from a deflated configuration to an inflated configuration when filled with the gas formed during the cell formation process of the battery cell 20.

Current practices to analyze the quality of battery cells 20 involves performing a discharge capacity check (i.e., checking that the cell provides capacity (measured in amp-hours) that is within a determined specification) or performing an inventory hold and open circuit voltage (OCV) monitoring (which involves holding the inventory and checking for a decrease in OCV over time). While effective, such quality control measures are time intensive (with the potential for large quality spills and the added cost of overhead to store inventory) and data poor (i.e., not diagnostic or prognostic).

Data can be derived from the formation, beginning of life capacity checks, and cell manufacturing tracing as a way to perform efficient line quality checks. For example, data relating to the formation charge of the battery cell 20 and the discharge check of the cell may be utilized. More specifically, pattern recognition of formation cycle data combined with the discharge check in an accelerated cycling test (ACT) to create a learning feedback. ACT is a short-term aging and cycling test to determine if the candidate cell of a particular lot of cells meets durability requirements based on 100 to 300 charge and discharge cycles and is delayed because quality control (QC) checks are not combined during the time-consuming formation protocol. Feedback identified during the cell formation cycle has been identified to provide for more timely corrective action during cell fabrication. Definitive quality checks earlier in the manufacturing process reduce the need for cell and pack storage to conduct voltage droop testing. Data rich process monitoring improves cell quality and is cost effective when done during the assembly's rate limiting step. Data processing using advanced analytics is used to generate and monitor key features of the electrochemical signature. Examples of analyzing the data relating to the formation charge of the battery cell 20 and the discharge check are shown and described in U.S. patent application Ser. No. 17/350,620, simultaneously filed on Jun. 17, 2021 and entitled "ELECTROCHEMICAL METHODS FOR IDENTIFICATION OF CELL QUALITY," the disclosure of which is hereby incorporated by reference.

The gas produced by the cell formation process can also provide data that may be used to assess the quality of the battery cell 20. The excessive production of gas can be indicative of a low-quality battery cell 20. More specifically, in one example the battery cell 20 is expected to produce between 0.5 to 3 mL of gas per Ah of nominal capacity. If the amount of gas produced is greater than 3 mL/Ah nominal capacity or less than 0.5 mL/Ah nominal capacity, the battery cell 20 may be low-quality. The excessive gas may be due to several reasons. As one example, the complete inactivity of electrolyte additives such as vinyl carbonate (VC), vinyl ethylene carbonate (VEC), etc. will lead to excessive consumption of ethylene carbonate (EC) resulting in gas production. In this situation, these battery cells 20 show very poor charge retention with cycling. Poor additive performance due to partial expiration and degradation will also lead to excessive EC consumption and increased gas generation volume though not to the extent as seen in the previous example.

In general, small gas volume results in the highest initial charge capacity of the battery cell 20, while an increase in gas volume (due to EC reduction) is correlated to degradation of charge capacity over time. Excessive Ethylene Carbonate (EC) reduction during the formation cycle consumes lithium salt in the electrolyte, which lowers the total available "lithium inventory" in the battery cell 20, which reduces ultimate charge capacity. Poor electrolyte additive performance causes a more rapid breakdown of the SEI layer. As a result, additional EC reduction is necessary to maintain the SEI layer. The SEI layer formed primarily from EC reduction has poor mechanical properties and greater thickness, which is inferior to one formed when electrolyte additives are present.

Examples of measuring and analyzing the data relating to the volume of the gas produced during the formation charge of the battery cell 20 are shown and described in U.S. patent application Ser. No. 17/350,644, simultaneously filed on Jun. 17, 2021 and entitled "QUALITY CONTROL SYSTEM FOR ANALYZING THE QUALITY OF A BATTERY CELL THROUGH A VOLUMETRIC MEASUREMENT OF GAS FORMED DURING A CELL FORMATION PROCESS AND A METHOD OF ANALYZING THE SAME," the disclosure of which is hereby incorporated by reference.

Furthermore, the composition of the gas provides data that can be used to assess the quality of the battery cell 20. For example, certain substances are consistently found in the gas pouch 26 after the cell formation process. Those substances include methane, ethene, ethane, butane and isomers thereof, hydrogen, carbon monoxide, and carbon dioxide. The individual compositions of those substances may be indicative of quality defects during the cell formation process, such as no additives, humidity, aged electrolyte, and lean electrolyte. Furthermore, the cumulative amount of the substances may be greater than a threshold and indicative of a low-quality battery cell 20. Examples of measuring and analyzing the data relating to the composition of the gas produced during the formation charge of the battery cell 20 are shown and described in U.S. patent application Ser. No. 17/350,650, simultaneously filed on Jun. 17, 2021 and entitled "QUALITY CONTROL SYSTEM FOR ANALYZING THE QUALITY OF A BATTERY CELL THROUGH ANALYSIS OF A PHYSICAL PROPERTY OF A GAS FORMED DURING A CELL FORMATION PROCESS AND A METHOD OF ANALYZING THE SAME," the disclosure of which is hereby incorporated by reference.

Figure 3:
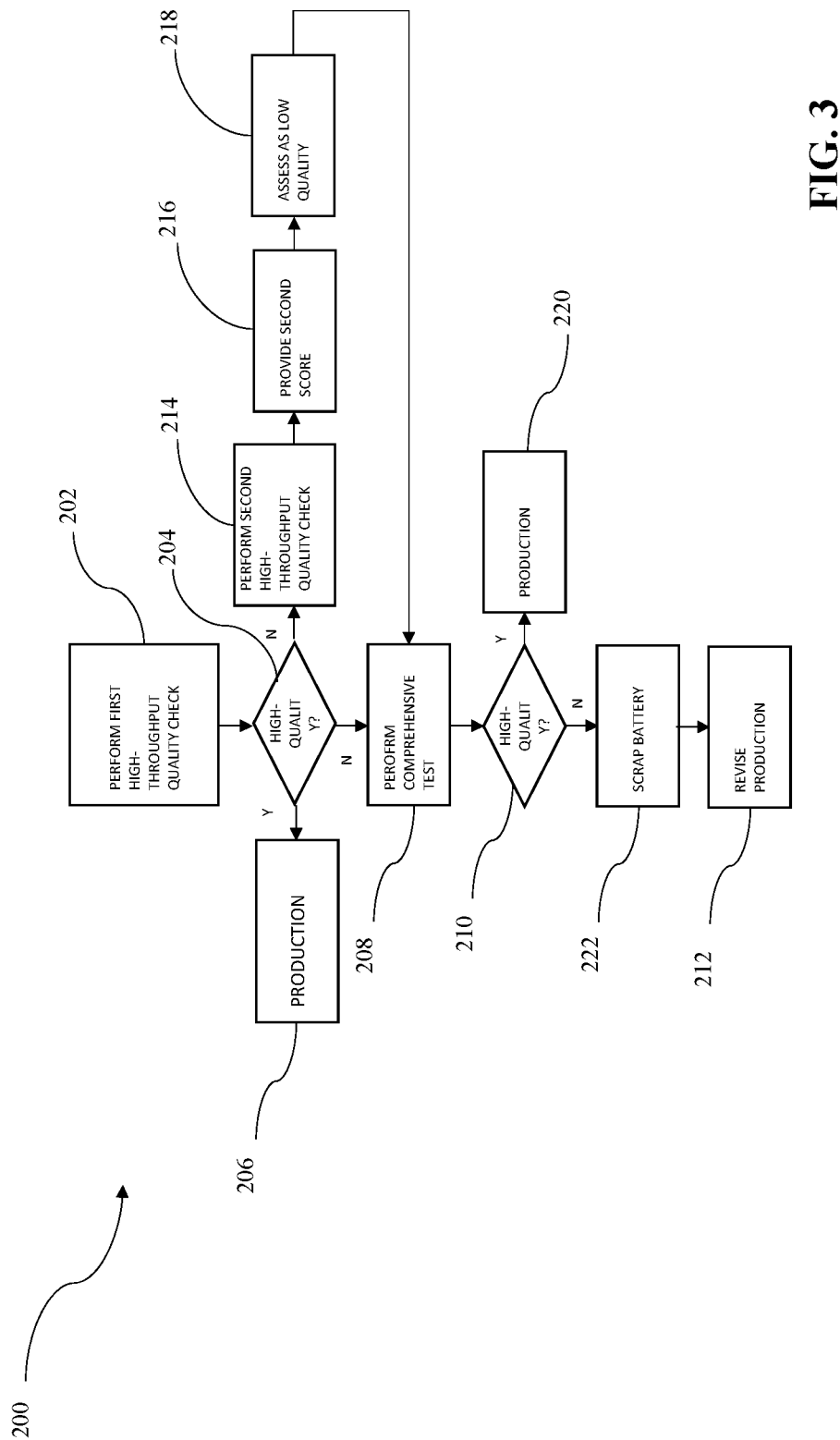
FIG. 3 is a flow chart of one example of a method of analyzing the quality of the battery cell.

According to several aspects of the present disclosure, a method 200 of analyzing the quality of the battery cell 20 is disclosed herein and shown in FIG. 3. The method comprises performing a high-throughput quality check on the battery cell 20 with a quality control system as shown in box 202, assessing a quality score to the battery cell 20 as shown in box 204, with a quality score identifying the battery cell 20 as low-quality or high-quality. If the battery cell 20 is identified as high-quality, the method further comprises reintroducing the battery cell 20 into production as shown in box 206. The method further comprises performing a comprehensive quality check on the battery cell 20 if identified as low-quality as shown in box 208. The method further comprises assessing an enhanced quality score to the battery cell 20 superseding the quality score of the quality control system identifying the battery cell 20 as confirmed low-quality or confirmed high-quality as shown in box 210 and providing revised production instructions for manufacturing successive battery cells 20 if confirmed low-quality as shown in box 212.

The high-throughput quality check on the battery cell 20 with the quality control system provides a way to perform efficient line quality checks. More specifically, performing the high-throughput quality check on the battery cell 20 with the quality control system as shown in box 202 may be further defined as one of analyzing the cell formation charge data of the battery cell 20, analyzing the volume of gas within the gas pouch 26 of the battery cell 20, analyzing the composition of the gas within the gas pouch 26, and analyzing the battery cell 20 discharge check data, which have been described above and incorporated into this application by reference. As mentioned above, current ways of checking the quality of a battery cell 20 require inventory holds for lot acceptance test (LAT) that involve holding the inventory and checking for a decrease in OCV over time. Current OCV checks require a hold of up to seven days. As such, the term "high-throughput" can mean less than seven days. However, in general, the amount of time is less than that, with most of the above-mentioned processes being performed within a matter of minutes, or (in some cases) a matter of seconds.

The terms "high-quality" and "low-quality" refer in-part to the ability of the battery cells 20 to hold a charge. As mentioned above, the ability of the battery to hold the charge is at least partly related to the cell formation process and, moreover, whether the SEI properly formed on the electrode. The processes described above in their respective applications provide ways of collecting data that analyze whether the battery cell 20 can hold a charge, whether the SEI was properly formed, or both. This data is analyzed in view of threshold values, from which a designation of quality is derived.

A computational system may be utilized by the method. The computational system may comprise at least one processor and a memory comprising program instructions. The memory may be further defined as a non-transitory computer-readable medium which includes, but is not limited to, random access memory (RAM), hard disk drive, and a flash drive. The computational system may be utilized to perform each of the steps of the method described herein. For example, the processor may perform the high-throughput quality check from instructions from the memory. Data collected from the high-throughput quality check may also be analyzed by the processor and compared to stored information (such as a threshold value) in the memory. The processor may assess the quality score based on the analysis. As another example, the processor may perform the comprehensive quality check on the battery cell from instructions from the memory. Data collected from the comprehensive quality check may also be analyzed by the processor and compared to stored information (such as a threshold value) in the memory. The processor may assess the enhanced quality score based on the analysis. The processor may further provide the revised production instructions for manufacturing successive battery cells. It is to be appreciated the computational system may be utilized at any step in the method such that some or all of the method is automated.

The quality control system may be further defined as a first quality control system and the quality score may be further defined as a first quality score. The method may further comprise performing a high-throughput quality check on the battery cell 20 with a second quality control system as shown in box 214 further defined as one of analyzing the cell formation charge data of the battery cell 20, analyzing the volume of gas within the gas pouch 26 of the battery cell 20, analyzing composition of the gas within the gas pouch 26, and analyzing the battery cell 20 discharge check data that was not performed by the first quality control system, and assessing a second quality score to the battery cell 20 as shown in box 216, with second quality score identifying the battery cell 20 as low-quality or high-quality. The method may further comprise analyzing the first and second quality scores and assessing a global quality score identifying the battery cell 20 as low-quality or high-quality as shown in box 218. Assessing the global quality score occurs prior to performing the comprehensive quality check on the battery cell 20. The global quality score averages the quality scores of the first and second quality control systems. As such, the second quality control system can adjust the position of the quality score of the first quality control system (i.e., raise or lower the quality score). This scales the two quality scores and provides a clearer assessment of the quality of the battery cell 20.

In one example, performing the high-throughput quality check on the battery cell 20 with the first quality control system as shown in box 202 is further defined as analyzing the cell formation charge data of the battery cell 20 and performing the high-throughput quality check on the battery cell 20 with the second quality control system as shown in box 214 is further defined as analyzing the composition of the gas within the gas pouch 26, wherein analyzing the cell formation charge data of the battery cell 20 occurs prior to analyzing the composition of the gas within the gas pouch 26. The electrochemical signals can be indicative of which gasses are being generated and in what amount. Furthermore, the gas analysis can be used to corroborate these results and search for additional information as to root cause of defects.

In another example, performing the high-throughput quality check on the battery cell 20 with the first quality control system as shown in box 202 is further defined as analyzing the cell formation charge data of the battery cell 20 and wherein performing the high-throughput quality check on the battery cell 20 with the second quality control system as shown in box 214 is further defined as analyzing the volume of gas within the gas pouch 26 of the battery cell 20, wherein analyzing the cell formation charge data of the battery cell 20 occurs prior to analyzing the volume of gas within the gas pouch 26 of the battery cell 20. The electrochemical signatures can be indicative of the amount of gas generated. The methods of gas volume estimation can be used to as verification and may assist in root cause analysis.

In another example, performing the high-throughput quality check on the battery cell 20 with the first quality control system as shown in box 202 is further defined as analyzing the cell formation charge data of the battery cell 20 and wherein performing the high-throughput quality check on the battery cell 20 with the second quality control system as shown in box 214 is further defined as analyzing the battery cell 20 discharge check data, wherein analyzing the cell formation charge data of the battery cell 20 occurs prior to analyzing the battery cell 20 discharge check data. The analysis of beginning of life capacity check discharge curves can be used as another check of cell quality and distinguish formation conditions likely to lead to better long term cell performance.

In one example, performing the comprehensive quality check on the battery cell 20 if identified as low-quality as shown in box 208 is further defined as performing gas chromatography on the gas within the gas pouch 26. In another example, performing the comprehensive quality check on the battery cell 20 if identified as low-quality as shown in box 208 is further defined as performing ACT through aging and repeated charge and discharge cycling. Furthermore, both performing gas chromatography on the gas within the gas pouch 26 and performing ACT through aging and repeated charge and discharge cycling may occur on the battery cell 20. To perform gas chromatography, the gas within the gas pouch 26 is removed from the gas pouch 26 and passed through a gas chromatograph. Gas chromatography is the process of separating compounds in gas disposed within the gas pouch 26, allowing for a thorough analysis of the composition of the gas. The composition of the gas in the low-quality battery cell 20 can be compared to a known composition found healthy battery cell 20. The deviations in the composition may be used to determine the root cause of the low-quality battery cell 20 (e.g., no additives, lean electrolyte, aged electrolyte, humidity, etc.). While gas chromatography provides a more thorough analysis of the battery cell 20, gas chromatographs usually have substantial cost to own and operate and require lengthier time to analyze the gas compared to the times required to by the quality control systems described above. Furthermore, the lengthy cycles performed during ACT provide a more accurate assessment of the ability of the battery cell 20 to hold a charge. However, ACT requires up to 5 months to perform, as described above. As such, the quality control systems described above provide an accurate way of screening the battery cells 20 for quality, with the comprehensive quality check performed by gas chromatography, LAT, etc. performing a thorough analysis of the battery cells 20 deemed low-quality.

In one example, providing revised production instructions for manufacturing successive battery cells 20 if confirmed low-quality as shown in box 212 is further defined as providing instructions for adaptive formation charge parameters. Adaptive formation charge parameters refer to performing corrective action to the cell formation process. More specifically, data from the cell formation process (such as voltage, current, pressure and temperature versus time) is monitored in real time and (if necessary) corrective actions on the formation schedule could be implemented to ensure desired SEI formation based upon feedback from the comprehensive quality check. Corrective action may include the processor of the computational system (or another computational system within a network) instructing a power supply to apply a corrected constant current or hold a corrected first and/or second voltage limit for a subsequent battery cell 20 during the cell formation process. The computational system may also instruct a temperature control module to correct the ambient temperature of the subsequent battery cell 20 (e.g., with a heater and/or an air conditioner) during the cell formation process. The data from the cell formation process, along with the analysis result from the comprehensive quality check and modified actions to the cell formation process may be archived in a networked repository. Information from this repository could be used to further analyze cell quality down the manufacturing line.

Based on metadata analysis using the data streams described above, the method allows for distinguishing (with high certainty) difference between best performing unacceptable (low-quality) battery cell 20 and lowest performing acceptable (high-quality) battery cell 20. The battery cell 20 may include an identifier (such as a bar code) that may be traceable, from which information from the quality data may be accessed. Based on a composite score of these data streams cells can be binned according to performance (e.g., high, medium, and low) or rejected as defective. The meta and raw data from the rejected cells may be subject to escalation analysis to determine root cause of the defect. Furthermore, tracing of raw material lots and other processing monitoring can be used to identify other battery cells 20 in the defective cell cohort (which may also have this defect) for quarantine and possible remediation processing to correct errors.

The method 200 may further comprise reintroducing the battery cell 20 into production if the battery cell 20 is confirmed high-quality as shown in box 220. More specifically, if the battery cell 20 is found to have a quality that falls within a desired specification, the battery cell 20 may be placed back into production and sold individually, as part of the battery pack, or in any other configuration. On the other hand, the method 200 may further comprise scrapping the battery cell 20 if the battery cell 20 is confirmed low-quality as shown in box 222 (i.e., permanently removing the battery cell 20 from production). The battery cell 20 may be disassembled and components may be utilized for recycling. Furthermore, the battery cell 20 may re-used in other non-vehicle applications, such as stationary power applications.

Accordingly, the method 200 of analyzing the quality of the battery cell 20 offers several advantages. Checking the quality of the battery cell 20 during and/or after the cell formation process reduces the need to perform lengthy inventory holds and OCV monitoring as currently practiced, which increases manufacturing throughput. Furthermore, the comprehensive quality check on battery cells 20 previously identified as low-quality allows for a more effective root-cause analysis.

The description of the present disclosure is merely exemplary in nature and variations that do not depart from the general sense of the present disclosure are intended to be within the scope of the present disclosure. Such variations are not to be regarded as a departure from the spirit and scope of the present disclosure.

What is claimed is:

1. A method of analyzing a quality of a battery cell, the method comprising:
   performing a first high-throughput quality check on the battery cell with a quality control system, wherein the first high-throughput quality check is selected from the group consisting of analyzing a cell formation charge data of the battery cell, analyzing a volume of a gas within a gas pouch of the battery cell, analyzing a composition of the gas within the gas pouch, and analyzing a battery cell discharge check data;
   assessing a first quality score to the battery cell identifying the battery cell as low-quality or high-quality, wherein the first quality score is related to an estimated charge quantity of the battery cell based on the first high-throughput quality check;
   performing a comprehensive quality check on the battery cell when identified as low-quality by the first quality score, wherein the comprehensive quality check is selected from the group consisting of performing gas chromatography on the gas within the gas pouch of the battery cell identified as low-quality and performing accelerated cycle testing (ACT) through aging and repeated charge and discharge cycling of the battery cell identified as low-quality;
   assessing an enhanced quality score to the battery cell based on the comprehensive quality check, with the enhanced quality score identifying the battery cell as low-quality or high-quality and the enhanced quality score representing a more accurate estimated charge quantity of the battery cell than the first quality score, wherein the enhanced quality score supersedes the first quality score; and providing revised production instructions for manufacturing successive battery cells when the enhanced quality score identifies the battery cell as low-quality.

2. The method of claim 1, further comprising: performing a second high-throughput quality check on the battery cell with a second quality control system, wherein the second quality control system is selected from the group consisting of analyzing the cell formation charge data of the battery cell, analyzing the volume of gas within the gas pouch of the battery cell, analyzing the composition of the gas within the gas pouch, and analyzing the battery cell discharge check data that was not performed by the first quality control system, and wherein the second quality control system is different than the first quality control system; and assessing a second quality score to the battery cell, with second quality score identifying the battery cell as low-quality or high-quality, wherein the second quality score is related to an estimated charge quantity of the battery cell based on the second high-throughput quality check.

3. The method of claim 2 further comprising averaging the first quality score and the second quality score to generate a global quality score, wherein the global quality score identifies the battery cell as low-quality or high-quality, the global quality score representing a more accurate estimated charge quantity of the battery cell than the first quality score and the second quality score individually.

4. The method of claim 3 wherein the enhanced quality score is assessed when the global quality score identifies the battery cell as low-quality, the enhanced quality score represents a more accurate estimated charge quantity of the battery cell than the global quality score, wherein the enhanced quality score supersedes the global quality score.

5. The method of claim 3 wherein performing the first high-throughput quality check on the battery cell with a first quality control system is further defined as analyzing the cell formation charge data of the battery cell and wherein performing the second high-throughput quality check on the battery cell with the second quality control system is further defined as analyzing the composition of the gas within the gas pouch, wherein analyzing the cell formation charge data of the battery cell occurs prior to analyzing the composition of the gas within the gas pouch.

6. The method of claim 3 wherein performing the first high-throughput quality check on the battery cell with a first quality control system is further defined as analyzing the cell formation charge data of the battery cell and wherein performing the second high-throughput quality check on the battery cell with the second quality control system is further defined as analyzing the volume of gas within the gas pouch of the battery cell, wherein analyzing the cell formation charge data of the battery cell occurs prior to analyzing the volume of gas within the gas pouch of the battery cell.

7. The method of claim 3 wherein performing the first high-throughput quality check on the battery cell with a first quality control system is further defined as analyzing the cell formation charge data of the battery cell and wherein performing the second high-throughput quality check on the battery cell with the second quality control system is further defined as analyzing the battery cell discharge check data, wherein analyzing the cell formation charge data of the battery cell occurs prior to analyzing the battery cell discharge check data.

8. The method of claim 1 wherein providing revised production instructions for manufacturing successive battery cells if confirmed low-quality is further defined as providing instructions for adaptive formation charge parameters.

9. The method of claim 1 further comprising reintroducing the battery cell into production if the battery cell is confirmed high-quality.

10. The method of claim 1 further comprising scrapping the battery cell if the battery cell is confirmed low-quality.

11. A method of analyzing a quality of a battery cell, the method comprising:
performing a first high-throughput quality check on the battery cell with a first quality control system, wherein the first high-throughput quality check is selected from the group consisting of analyzing a cell formation charge data of the battery cell, analyzing a volume of a gas within a gas pouch of the battery cell, analyzing a composition of the gas within the gas pouch, and analyzing a battery cell discharge check data;
assessing a first quality score to the battery cell identifying the battery cell as low-quality or high-quality, wherein the first quality score is related to an estimated charge quantity of the battery cell based on the first high-throughput quality check;
performing a second high-throughput quality check on the battery cell with a second quality control system, wherein the second quality control system is selected from the group consisting of analyzing the cell formation charge data of the battery cell, analyzing the volume of gas within the gas pouch of the battery cell, analyzing the composition of the gas within the gas pouch, and analyzing the battery cell discharge check data that was not performed by the first quality control system, and wherein the second quality control system is different than the first quality control system;
assessing a second quality score to the battery cell, with the second quality score identifying the battery cell as low-quality or high-quality, wherein the second quality score is related to an estimated charge quantity of the battery cell based on the second high-throughput quality check;
averaging the first and second quality scores to generate a global quality score identifying the battery cell as low-quality or high-quality;
performing a comprehensive quality check on the battery cell when the global quality score is low-quality, wherein the comprehensive quality check is selected from the group consisting of performing gas chromatography on the gas within the gas pouch of the battery cell identified as low-quality and performing accelerated cycle testing (ACT) through aging and repeated charge and discharge cycling of the battery cell identified as low-quality;
assessing an enhanced quality score to the battery cell based on the comprehensive quality check, with the enhanced quality score identifying the battery cell as low-quality or high-quality and the enhanced quality score representing a more accurate estimated charge quantity of the battery cell than the global quality score, wherein the enhanced quality score supersedes the global quality score; and
providing instructions for adaptive formation charge parameters when the enhanced quality score identifies the battery cell as low-quality.

12. The method of claim 11 wherein assessing the global quality score occurs prior to performing the comprehensive quality check on the battery cell.

13. The method of claim 11 further comprising scrapping the battery cell if the battery cell is confirmed low-quality.

* * * * *